United States Patent
Case et al.

(10) Patent No.: US 7,871,434 B2
(45) Date of Patent: Jan. 18, 2011

(54) PERCUTANEOUSLY DEPLOYED VASCULAR VALVES

(75) Inventors: Brian C. Case, Bloomington, IN (US); Charles W. Agnew, West Lafayette, IN (US); Jacob A. Flagle, Indianapolis, IN (US)

(73) Assignee: Cook Incorporated, Bloomington, IN (US)

( * ) Notice: Subject to any disclaimer, the term of this patent is extended or adjusted under 35 U.S.C. 154(b) by 1109 days.

(21) Appl. No.: 10/551,399

(22) PCT Filed: Apr. 1, 2004

(86) PCT No.: PCT/US2004/009971

§ 371 (c)(1),
(2), (4) Date: Aug. 8, 2006

(87) PCT Pub. No.: WO2004/089253

PCT Pub. Date: Oct. 21, 2004

(65) Prior Publication Data

US 2007/0027518 A1    Feb. 1, 2007

Related U.S. Application Data

(60) Provisional application No. 60/459,475, filed on Apr. 1, 2003.

(51) Int. Cl.
*A61F 2/24* (2006.01)
*A61F 2/06* (2006.01)
(52) U.S. Cl. .............. 623/2.12; 623/2.13; 623/2.14; 623/2.18; 623/1.24; 623/1.26
(58) Field of Classification Search .......... 623/1.24, 623/1.32, 1.36, 2.12, 2.13, 2.16
See application file for complete search history.

(56) References Cited

U.S. PATENT DOCUMENTS

| | | | |
|---|---|---|---|
| 4,218,782 A | | 8/1980 | Rygg |
| 4,902,508 A | | 2/1990 | Badylak et al. |
| 4,994,077 A | * | 2/1991 | Dobben ............... 623/2.2 |
| 5,156,620 A | | 10/1992 | Pigott |
| 5,411,552 A | | 5/1995 | Andersen et al. |
| 5,554,389 A | | 9/1996 | Badylak et al. |
| 5,607,465 A | | 3/1997 | Camilli |
| 5,843,170 A | * | 12/1998 | Ahn ..................... 623/1.34 |
| 5,855,601 A | | 1/1999 | Bessler et al. |
| 5,993,844 A | | 11/1999 | Abraham et al. |
| 6,099,567 A | | 8/2000 | Badylak et al. |
| 6,110,201 A | | 8/2000 | Quijano et al. |
| 6,126,686 A | | 10/2000 | Badylak et al. |
| 6,168,614 B1 | | 1/2001 | Andersen et al. |
| 6,200,336 B1 | | 3/2001 | Pavcnik et al. |
| 6,206,931 B1 | | 3/2001 | Cook et al. |
| 6,254,636 B1 | | 7/2001 | Peredo |
| 6,287,334 B1 | | 9/2001 | Moll et al. |

(Continued)

FOREIGN PATENT DOCUMENTS

WO    WO 00/64381    11/2000

(Continued)

*Primary Examiner*—Alvin J Stewart
*Assistant Examiner*—Yashita Sharma
(74) *Attorney, Agent, or Firm*—Woodard, Emhardt, Moriarty, McNett & Henry LLP

(57) ABSTRACT

Described are percutaneous vascular valves (11) free of attached support structures and deployment systems (31) and methods for providing attachment of the valves within a vascular vessel.

27 Claims, 9 Drawing Sheets

U.S. PATENT DOCUMENTS

| | | |
|---|---|---|
| 6,299,637 B1 | 10/2001 | Shaolian et al. |
| 6,364,905 B1 | 4/2002 | Simpson et al. |
| 6,485,723 B1 | 11/2002 | Badylak et al. |
| 6,508,833 B2 | 1/2003 | Pavcnik et al. |
| 6,582,462 B1 | 6/2003 | Andersen et al. |
| 6,716,241 B2 | 4/2004 | Wilder et al. |
| 6,752,828 B2 | 6/2004 | Thornton et al. |
| 2001/0011187 A1 | 8/2001 | Pavcnik et al. |
| 2001/0039450 A1 | 11/2001 | Pavcnik et al. |
| 2002/0123800 A1 | 9/2002 | Taheri et al. |
| 2002/0138138 A1* | 9/2002 | Yang ................... 623/2.18 |
| 2002/0169456 A1 | 11/2002 | Tu et al. |
| 2002/0188348 A1 | 12/2002 | DiMatteo et al. |
| 2003/0036795 A1 | 2/2003 | Andersen et al. |
| 2003/0130726 A1 | 7/2003 | Thorpe |
| 2003/0191525 A1 | 10/2003 | Thornton |
| 2003/0208261 A1 | 11/2003 | Thorpe et al. |
| 2004/0015230 A1 | 1/2004 | Moll et al. |
| 2004/0049262 A1 | 3/2004 | Obermiller et al. |
| 2004/0087975 A1* | 5/2004 | Lucatero et al. ............ 606/139 |
| 2004/0193253 A1 | 9/2004 | Thorpe et al. |
| 2009/0157169 A1* | 6/2009 | Pavcnik et al. ............ 623/1.24 |

FOREIGN PATENT DOCUMENTS

| | | |
|---|---|---|
| WO | WO 01/19285 | 3/2001 |
| WO | WO 01/64137 | 9/2001 |
| WO | WO 03/002165 | 1/2003 |
| WO | WO 03/070124 | 8/2003 |

* cited by examiner

PERCUTANEOUSLY DEPLOYED VASCULAR VALVES

REFERENCE TO RELATED APPLICATIONS

The present application is a national stage of International Patent Application PCT/US23004/009971 filed Apr. 1, 2004, which claims the benefit of U.S. Provisional Application No. 60/459,475 filed Apr. 1, 2003, all of which are hereby incorporated by reference.

BACKGROUND

The present invention resides generally in the field of medical devices, and more particularly relates to artificial valve devices such as those implanted within the vascular system.

As further background, in all vertebrates, blood is transported away from the heart and throughout the body via arteries and returns to the heart through veins. To allow for optimal transport back to the heart and to reduce blood pressure build-up, veins contain various valves within their lumens, which open to permit blood flow to the heart but close to prevent the backflow of blood. Accordingly, venous valves function to provide the unidirectional flow of blood back to the heart.

Problems can arise when these venous valves fail to function properly. For example, venous valves can become incompetent or damaged by disease such that the backflow of blood is not prevented. When this occurs, blood pressure builds up and the veins and their valves become dilated, particularly in the lower extremities. If enough pressure builds up, the condition of venous insufficiency may develop. The severity of this condition is substantial, resulting in swelling, extensive pain, deformities, and, in the most severe cases, the development of ulcers can occur. If these ulcers become infected, amputation may ultimately be necessary to save the patient's life.

Currently, there is no proven cure for venous insufficiency. Basic treatments include elevation of the legs or the use of compression stockings. If surgery is determined to be necessary, vein stripping is typically performed, which involves the removal of the incompetent or damaged vein(s). Other surgical methods involve valvular reconstruction or transplantation.

Recently, the development of artificial and biological valves has been employed in an attempt to return normal pressure to the veins. There are a variety of these valves described in the art, which are generally designed to allow normal flow of blood back to the heart, while preventing retrograde flow. For example, U.S. Pat. No. 6,508,833 discloses a multiple-sided medical device comprising a closed frame of a single piece of wire or other resilient material and having a series of bends and interconnecting sides. The device has both a flat configuration and a second, folded configuration that comprises a self-expanding frame. The device is pushed from a delivery catheter into the lumen of a duct or vessel. A covering of fabric or other flexible material is sutured or attached to the frame to form an artificial valve. The flexible material utilized in the disclosed valves can be comprised of collagenous submucosa obtained from various animals, such as, for example, pigs, cattle, and sheep. This material can be processed and preserved so as to be capable of inducing host tissue proliferation, remodeling, and regeneration of appropriate tissue structures e.g., veins upon implantation in vivo (see, e.g., U.S. Pat. No. 6,485,723). The preparation of submucosal material is generally described in U.S. Pat. Nos. 4,902,508 and 5,554,389. The submucosal material can be prepared in large, flat sheets, which are subsequently cut and attached to a framing element, for example a stent, for deployment in a vein.

Despite work in the area there remain needs for medical products and methods for grafting within the vasculature, including the venous system, to improve blood flow. Desirably, such products and methods could eliminate or minimize the need for the presence of implanted support structures such as stents or frames, associated with the engrafted or implanted product. Such support structures commonly exert significant radial force upon vessel walls, and in certain situations may migrate deleteriously into the walls and/or undesirably reduce the compliancy of the vessel in which they are implanted. As well, such stent or frame structures can present increased risks for thrombosis or embolism.

SUMMARY

In one embodiment, the present invention provides a vascular valve that comprises a stentless vascular valve body having at least one flexible or otherwise movable member for restricting blood flow. The flexible member has an edge for engaging a wall of a vascular vessel. The valve also includes wall-engaging adaptations located along the edge. The wall-engaging adaptations can include any suitable devices or materials such as barbs, adhesives, or the like. In preferred devices, the stentless vascular valve body is made with a remodelable material and in particular a remodelable extracellular matrix material.

In another embodiment, the invention provides a percutaneous vascular valve and delivery system. This system includes a stentless vascular valve body having at least one flexible or otherwise movable member for restricting blood flow, the flexible member having an edge for engaging a wall of a vascular vessel. This system further includes a percutaneous deployment device, wherein the deployment device has an expandable element adapted to force the edge against the vessel wall. Suitable stentless vascular valve bodies are as described above. Suitable percutaneous deployment devices may include a balloon catheter having adaptations for selectively forcing the edge against the vessel wall, and/or elongate devices having at least one expandable frame attached thereto with adaptations for expanding and contracting the frame while remaining attached to the elongate device. The stentless valve body may be releasably attached to the deployment device by any suitable means including by the use of adhesives or removable elements such as removable sutures.

The invention also provides a method for treating venous insufficiency, wherein the method includes deploying a stentless vascular valve body such as that described above so as to force the valve body against the vascular wall, and selectively attach edges of the valve body against the vascular wall, to seat the valve within the vein.

In another embodiment, the present invention provides a method for modifying blood flow in a vascular vessel. This method includes percutaneously delivering one or more pieces of flexible material to a site within a vascular vessel. The method further includes percutaneously attaching at least portions of the one or more pieces of flexible material to walls of the vascular vessel, so as to form a structure that selectively permits blood flow at a first direction and restricts blood flow in a second direction. Desirably, the flexible material in this embodiment will have remodelable properties, and may for example include a extracellular matrix material. In certain forms, the percutaneous attachment can be achieved by the delivery of energy to facilitate attachment of the portions of the flexible material to the wall. For example, this energy may activate a substance to bond the flexible material to the wall, and/or may weld the material to the wall as occurs in tissue welding applications.

Additional embodiments as well as features and advantages of the invention will be apparent to those skilled in the art from the descriptions herein.

DETAILED DESCRIPTION

Figure 1:
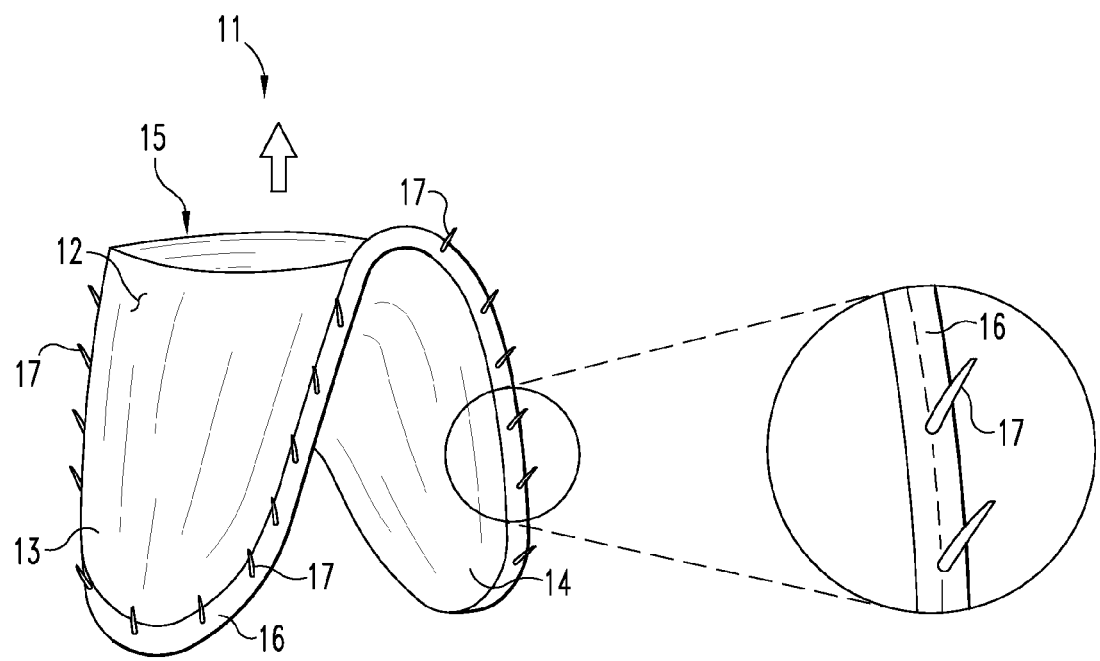
FIG. 1 provides a perspective view of one valve device of the invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

As disclosed above, the present invention provides vascular valve devices, and systems and methods for the delivery thereof.

With reference now to FIG. 1, shown is a perspective view of an illustrative valve device 11 of the present invention. Device 11 includes a stentless or frameless valve body formed of a flexible material 12, wherein in the illustrated embodiment the valve body includes a first leaflet 13 and a second leaflet 14. It will be understood in this regard that valve bodies having one leaflet, or a plurality of leaflets, e.g. two, three, four, five or more leaflets, are contemplated as within the scope of the present invention.

The valve body of device 11 includes an opening 15, configured to facilitate the valve function by selectively allowing blood flow in a first direction, and selectively restricting blood flow in a second direction opposite the first direction. Device 11 in particular is designed to facilitate net blood flow in the direction of the arrow. Leaflets 13 and 14 are formed with a flexible material and move outwardly to open the opening 15 when subjected to blood flow in the direction of the arrow, and move inwardly to close the opening 15 when subjected to blood flow in a direction opposite that of the arrow.

Device 11 also includes a lip 16 or other reinforcement along the edges of the leaflets 13 and 14. This lip 16 may be made from the same material or a different material than that of the leaflets 13 and 14. For example, lip 16 may be made by folding, rolling, or otherwise gathering and securing material at the periphery of material from which leaflets 13 and 14 are made. Alternatively, a different material may be secured to the periphery of leaflets 13 and 14 to provide the lip or other reinforcement. Still further, leaflets 13 and 14 may be integrally made with a reinforced lip 16, for example by molding, and/or material at the periphery of leaflets 13 and 14 may be treated to increase its strength relative to the remainder of leaflets 13 and 14, for example by adding crosslinking to the periphery where leaflets 13 and 14 are made of collagenous materials.

Lip 16 in the illustrated device incorporates adaptations for attachment to the vessel wall. For example, lip 16 can include a plurality of elements configured to partially or completely penetrate the vessel walls, for example barbs or hooks. Alternatively or in addition, lip 16 can be provided with a biocompatible adhesive sufficient to secure lip 16 to the vessel wall. A range of biocompatible and potentially also biodegradable adhesives are known and can be used in the present invention for this purpose. Lip 16 can be provided with the adhesive in any suitable manner, including for example a coating of adhesive on a surface of lip 16 that will come into contact with the vessel wall. As well, lip 16 can incorporate a sleeve or pocket (e.g. formed by folding back a portion of the material and attaching the edge to form a sleeve), and the sleeve or pocket can contain a biocompatible adhesive that will be released through openings such as slits or apertures in the sleeve upon compressing the lip 16 against the surface of the vessel wall. In still further embodiments of the invention, the adhesive can be applied in situ in the vessel the lip 16, and/or to corresponding areas of the vessel wall, using a catheter or other suitable delivery device.

Figure 1A:
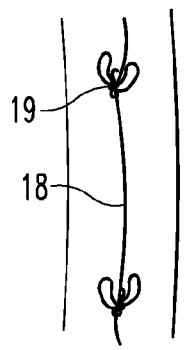
FIGS. 1a, 1b, and 1c illustrate various configurations of attachments of barbs to valve devices.
Figure 1B:
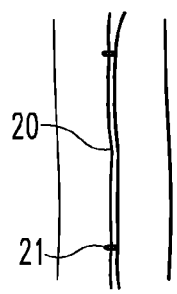
Figure 1C:
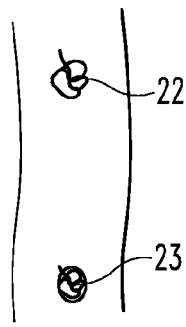

With reference now to FIGS. 1A-1C, shown are a number of ways to incorporate barbs into the lip 16 of the device 11. In FIG. 1A, barbs are provided with a suturable base, and each base is secured with individual suture knots 19 within a fold created along stitch line 18. In FIG. 1B, barbs are provided along a wire element 20, with each barb having a base 21 spaced from the others along the wire element 20. This wire element can similarly be stitched underneath a fold at the edge of leaflets 13 and 14, with the barbs penetrating the material at the edge of the leaflets 13 and 14. It will be understood that in this disclosed embodiment, this wire element does not constitute a stent, frame or other valve body support structure, as it does not serve to itself exert radial force upon the vessel walls to retain the position of the device, as would a stent. To the contrary, in certain embodiments, wire element 20 can be highly malleable, taking on the configuration to which it is forced, while not having sufficient resiliency or integrity to maintain significant radial force against a vessel wall. In FIG. 1C, each barb has a base 22 that is individually bonded to the periphery of the leaflets 13 and 14, for example with a suitable biocompatible adhesive. Still other means for securing barbs or similar attachment elements to the device 11 will be apparent to those skilled in the art given the teachings herein.

Figure 2:
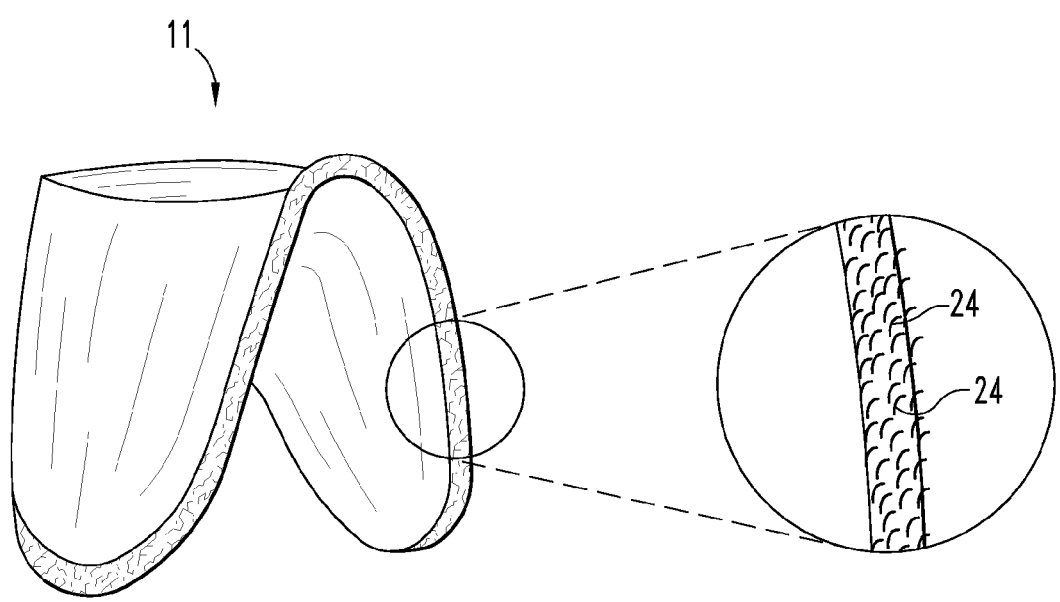
FIG. 2 provides a perspective view of another valve device of the invention.

Referring now to FIG. 2, shown is another embodiment of valve device 11, which is similar to that shown in FIG. 1 except in respect of the attachment elements along the periphery of the leaflets. In particular, FIG. 2 shows device 11 having a multitude of small, closely spaced vessel-wall-penetrating elements such as hooks 24 along the periphery of the valve body. To facilitate attachment, the small hooks or other penetrating elements are provided in a regular or irregular array along the lip of the device, particularly wherein the array includes hooks occurring generally longitudinally and laterally with respect to one another. That is, the array or swath of hooks or other elements along the periphery is desirably two or more hooks or elements wide, and as well extends longitudinally along the periphery. Further in this regard, it will be understood that the hooks or other penetrating elements such barbs can have a variety of sizes, orientations, and/or shapes. The individual elements can adopt a curved configuration and/or can have adaptations to cause them to resist withdrawal from the wall tissue once inserted therein, e.g. in the case of fish hook-type structures. As well, the penetrating elements can be oriented in differing directions from one another, for example utilizing multiple rows of either inward or outwardly facing barbs, or mixtures thereof. Such configurations for providing effective attachment to the walls, and resistance to withdrawal or migration, are contemplated as within the present invention. Further, the wall-penetrating elements can be provided by microbarbs, for example having a diameter in the range of about 0.005 inches to about 0.010 inches, but may be of any suitable diameter such as, but not limited to, about 0.0005 inches to about 0.10 inches. The lengths of such microbarbs may be any suitable length, typically in the range of between about 0.010 inches and about 0.100 inches, but may be of any suitable length including but not limited to about 0.001 inches to about 0.50 inches. The microbarbs can comprise a series of metallic wires or any other suitable material, or can be formed into a larger element by surface texturing techniques, such as ion texturing or EDM, or any other suitable method. The larger element can then be attached to the flexible material in any suitable manner. The microbarbs can be shaped to clutch the wall of the vessel at the implant site, with the shape including but not limited to a wedged shape where the tip of the wedge comes into contact with the vessel wall, or a curved or pointed or fish-hooked wire, or any other appropriate configuration.

It will also be understood that a combination of techniques can be used in the attachment of areas of the valve body to the vessel wall. Illustratively, the use of wall penetrating elements as discussed above can be made in combination with adhesive and/or tissue welding techniques as described further herein.

Figure 3:
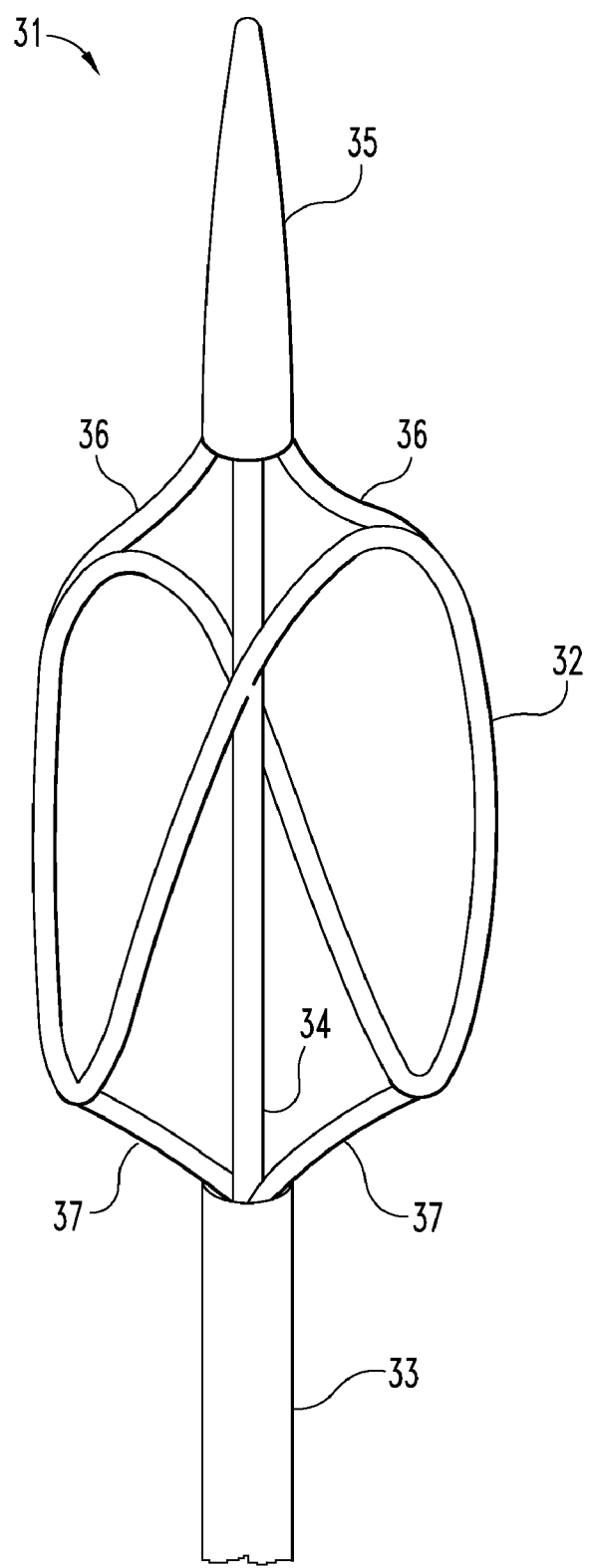
FIG. 3 provides a perspective view of one illustrative percutaneous deployment device of the invention.

FIG. 3 provides a perspective view of one illustrative percutaneous deployment device of the invention. Deployment device 31 generally includes an expandable frame 32 attached to an elongate member 34 such as a stylet, received within a lumenal device such as a catheter 33. Distal tip 35 of elongate member 34 is designed to be non-damaging to vessels in which it is to be deployed. A first end of frame 32 is connected at or near distal tip 35 by struts 36, and a second end of frame 32 is connected to member 34 at a more proximal location by struts 37. Frame 32 is shown in its expanded configuration, deployed by pushing the end of stylet 34 out of the end of catheter 33. Frame 32 of device 31 has wire or other frame elements configured to selectively force lip 16 against the vessel wall in a path extending longitudinally along and at least partially circumferentially around the vessel wall, e.g. in a generally serpentine pattern. Frame 32 can be retracted back into catheter 33 by pulling stylet 34 proximally, thus collapsing struts 37, frame 32 and struts 36 for receipt within catheter 33. The end opening of catheter 33 may be configured with a taper or other adaptation to facilitate collapse and receipt of these frame and strut elements, if desired. Additionally, in an alternate embodiment, proximal struts 37 can be attached to catheter 33, rather than stylet 34. In this fashion, frame 32 may reside externally of catheter 33 during the entire delivery and deployment operation. In this latter embodiment, where frame 32 is self-expanding, forcing the stylet 34 distally outward from the catheter will retain a collapsed frame configuration, and removing that force will allow frame 32 expansion. Where frame 32 is not self-expanding, it may be caused to expand by pulling stylet 34 proximally, and caused or allowed to regain a collapsed configuration by causing or allowing the stylet 34 to move distally.

Figure 4:
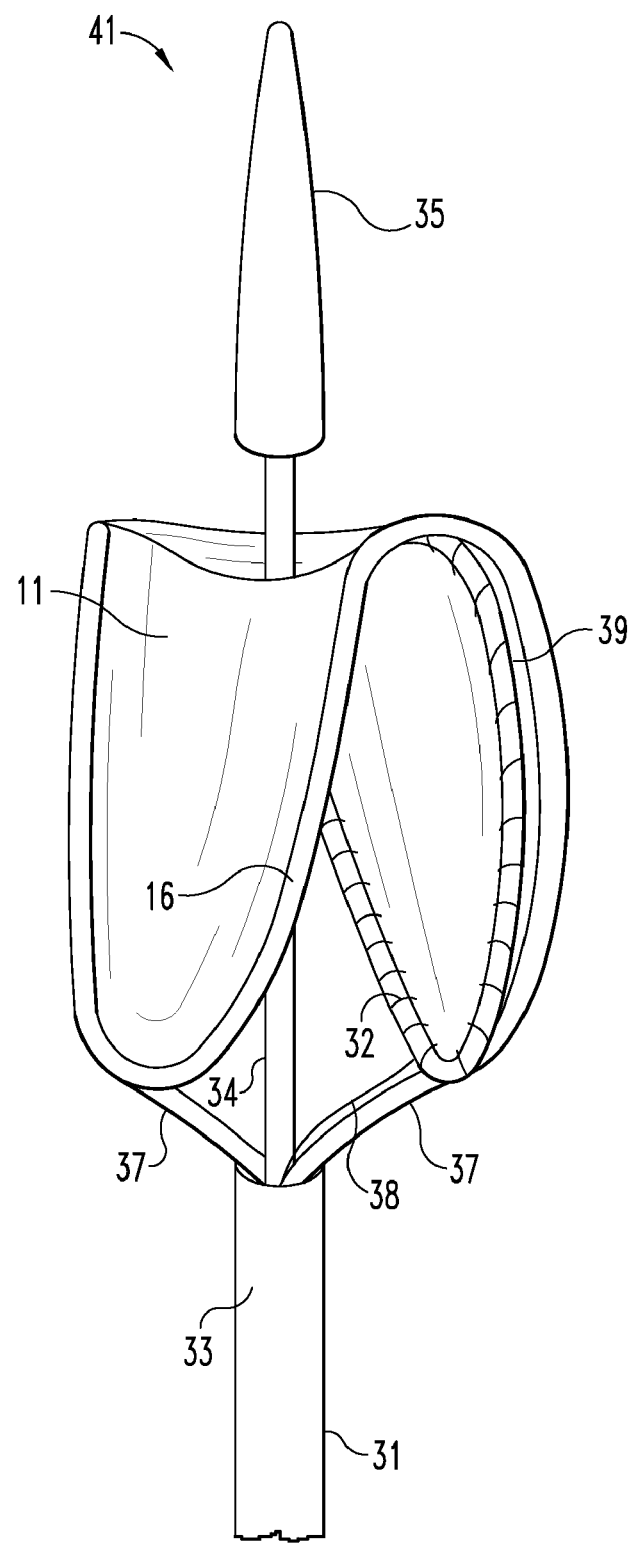
FIG. 4 provides a perspective view of a vascular valve deployment system having a valve body received upon the deployment device of FIG. 3.

With reference now to FIGS. 1-4 together, shown in FIG. 4 is a vascular valve deployment system 41 having a stentless valve body 11 (see FIG. 1 or 2) received upon deployment system 31 as shown in FIG. 3. In the illustrated system 41, valve body 11 is releasably attached to the frame 32 by a suture 38 wound through body 11 and around frame 32. Suture 38 extends into and through the lumen of catheter 32, such that a physician can pull and remove the suture 38 after deployment of the valve body 11 against the vessel wall. In this regard, other means for releasably retaining valve body 11 on frame 32 may also be used, including for example the use of tacky materials such as biocompatible polymers, e.g. a polyvinylpyrrolidone polymer. Suitable polyvinylpyrrolidone polymers that provide tack are known and commercially available, and can be used in the present invention. Other biocompatible adhesives are also known and can be used to temporarily or releasably secure lip 16 to frame 32.

Figure 5:
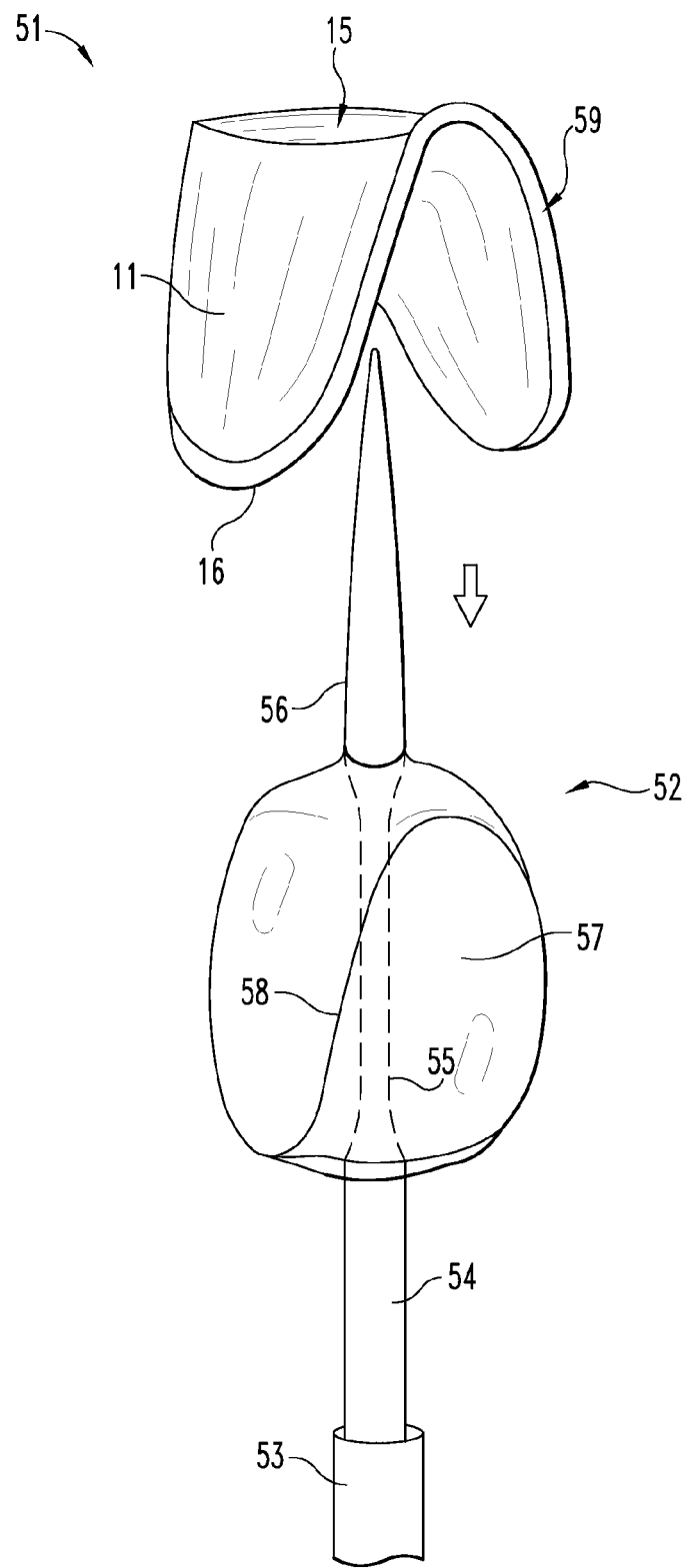
FIG. 5 provides a perspective view of another vascular valve deployment system of the invention.

Referring now to FIG. 5, shown is another vascular valve deployment system 51 of the invention, including an alternative expandable element for deployment of the valve body. System 51 includes a delivery device 52 including an outer sheath 53 and a delivery catheter 54 receivable therein. Delivery catheter 54 includes a relatively narrow section 55 underlying an inflatable balloon 57 expandable element, to facilitate receipt of the balloon 57, when deflated, into the outer sheath 53. Delivery catheter 54 also includes a distal tip 56 adapted to be non-damaging to the vascular vessel in which it is used.

Balloon 57 in the illustrative device includes adaptations that allow it to selectively force the lip 16 or edge of valve body 11 (see e.g. FIGS. 1 and 2) against the vessel wall. In the illustrated embodiment 51, balloon 57 adopts a predetermined shape upon inflation, the shape including at least one edge 58 configured to follow the lip 16 or other edge of valve body 11. A balloon that is partially or wholly non-compliant (e.g. having sufficient rigidity or stiffness, altogether or in appropriate areas, to inflate to the predetermined, regular shape) may be used for these purposes. In this manner, when balloon 57 is inflated, balloon edge 58 will force lip 16 against the vessel wall to secure the lip 16 to the vessel wall. As discussed hereinabove, barbs may be used to facilitate this attachment. In the illustrated system 51, a biocompatible adhesive 51 is incorporated along lip 16 for these purposes. In this regard, in certain forms of the invention, the biocompatible adhesive can be an activatable adhesive, such that once lip 16 is in position against the vessel wall, the adhesive can be activated to thereby attach the lip 16 to the vessel wall. For example, the adhesive can be an energy-activated adhesive, such as an adhesive activated by electromagnetic radiation, heat, or other energy sources. Illustratively, the adhesive can be an ultraviolet-light curable adhesive that is activated to bond the lip 16 to the vessel wall upon impingement by UV light. The UV light or other energy for activation of the adhesive can be provided by the delivery system itself by the incorporation of an appropriate energy source to deliver energy to the desired region(s), or can be applied using a separate probe or other instrument delivered to the implantation site either through the same percutaneous access or a different percutaneous access. In certain forms of the invention, where the valve device is delivered upon a balloon, a light-curable adhesive can be utilized and the balloon or adjacent regions of the delivery device can incorporate the light source, similar to that used in balloon devices currently used for photodynamic therapy.

Furthermore, in addition to the potential use of an adhesive to selectively attach areas of the valve material to the vessel wall, known tissue welding techniques can be used to attach those areas. As before, the energy can be provided by one or more sources built into the delivery structure, and/or can be provided by a probe delivered separately to the implant site either through the same percutaneous access or a different percutaneous access.

Illustratively, tissue welding within the vascular vessel can be conducted using laser welding techniques. For example, $CO_2$, Nd:YAG, THC:YAG, Argon, and near infrared diode lasers, can be used for these purposes. Such laser welds can also involve the use of substances to improve the weld strength (e.g. solders), including for example the application of proteins to the weld areas, including for instance fibrinogen, fibrin, albumin, or the like, or by the use of dyes such fluorescein, isothiocyanate, and indocyanine green, to enhance absorption of laser radiation at the site to be welded. Further in this regard, to improve the welding process, the areas of the valve body material to be welded to the vessel wall can contain collagen fibrils having free ends, wherein the free ends having a melting temperature below that of intact collagen fibrils included other areas of the valve body material. To achieve this, using a collagenous valve body material, the lip, edges or other desired areas of the flexible piece to be connected to the vessel wall can be treated with appropriate digestive or other agents to release collagen fibril free ends, and/or collagen fibers can be separately incorporated into these areas.

Other forms of energy can be also used in welding processes and/or adhesive activation processes, including for example microwave energy, radio frequency energy, ultraviolet light energy, and others. In each case, appropriate probes can be used to deliver the energy and/or such energy sources can be encompassed within the delivery system and configured to deliver energy to the desired sites, bands, or regions of attachment of the valve body to the vessel wall. Also in each case, for adhesive or welding purposes, an appropriate energy absorbing material that absorbs energy within a predetermined range of wavelengths or types, may be applied to the valve body to facilitate attachment.

The flexible or otherwise movable material (e.g., 12, FIG. 1) used in valve bodies of the invention is a biocompatible material, and is preferably a remodelable material. Suitable remodelable materials may be made from natural or synthetic polymers, and preferred materials comprise collagen. Thus, in general, the flexible material may comprise a material such as synthetic biocompatible polymers such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof; polylactic acid, polyglycolic acid or copolymers thereof, a polyanhydride, polycaprolactone, polyhydroxy-butyrate valerate, polyhydroxyalkanoate, or another biodegradable polymer.

In certain embodiments of the invention, the flexible material 12 is comprised of a naturally derived or synthetic collagenous material, and especially an extracellular matrix material. Suitable extracellular matrix materials include, for instance, submucosa (including for example small intestinal submucosa, stomach submucosa, urinary bladder submucosa, or uterine submucosa), renal capsule membrane, dura mater, pericardium, serosa, peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present invention, and their isolation and treatment, reference can be made to U.S. Pat. Nos. 4,902,508, 5,554,389, 5,993,844, 6,206,931, and 6,099,567. Renal capsule tissue can also be obtained from warm blooded vertebrates, as described more particularly in copending U.S. patent application Ser. No. 10/186,150 filed Jun. 28, 2002 and International Patent Application serial No. PCT/US02/20499 filed Jun. 28, 2002, published Jan. 9, 2003 as WO03002165. In addition, the flexible material employed in the invention may be provided as a single layer, or as a multilaminate structure. In this regard, techniques for laminating ECM or other collagenous layers can include fusing, crosslinking, bonding, suturing, or other suitable techniques. In certain aspects of the inventions, a multilaminate ECM or other collagenous structure can be used, wherein the attachment of adjacent layers is achieved at least in part using dehydrathermal bonding, for example induced by compressing or otherwise forcing layers against one another, and drying the layers. The drying can occur under heated conditions, under lyophilization conditions which may include freeze drying or evaporative cooling, under vacuum pressing conditions at room temperature or otherwise, and the like. Each of these may be combined with other techniques including chemical crosslinking and/or the use of suitable bonding agents such as glues or adhesives. As well, multilaminate structures, when used, can include layers of the same material, or of differing materials. Illustratively, the multilaminate structures can include at least two differing collagenous layers, e.g. in the case of laminating together two differing ECM materials.

In certain embodiments of the invention, the material used in the construction of the valve bodies of the invention can have adaptations that cause the material to resist attachment or incorporation into the vessel wall where such would be undesirable. For example, moveable portions of the valve body such as leaflet areas can incorporate or be coated with materials that decrease the likelihood of attachment or incorporation into the vessel walls. Illustratively, the moveable portions of the valve body can be coated with a synthetic polymer, including biodegradable synthetic polymers, over all or a portion of their exterior surfaces that will be exposed to contact to the vessel walls. Other areas of the moveable portions, including internal areas, could also bear such coatings. As well, the material in these areas can incorporate agents that improve resistant to attachment of incorporation into the vessel walls, including antiproliferative agents such as paclitaxel and other taxol derivatives, for example as disclosed in U.S. Pat. Nos. 5,157,049 and 5,616,608.

Frame elements 32, struts 36, 37, stylets 34, barbs 17, hooks 24, and other components of all embodiments of the present invention may also be made with any suitable biocompatible material. These include for example metals such as nitinol or other shape-memory materials, or stainless steel, as well as resorbable or nonresorbable polymeric materials, including those discussed above.

Figure 6:
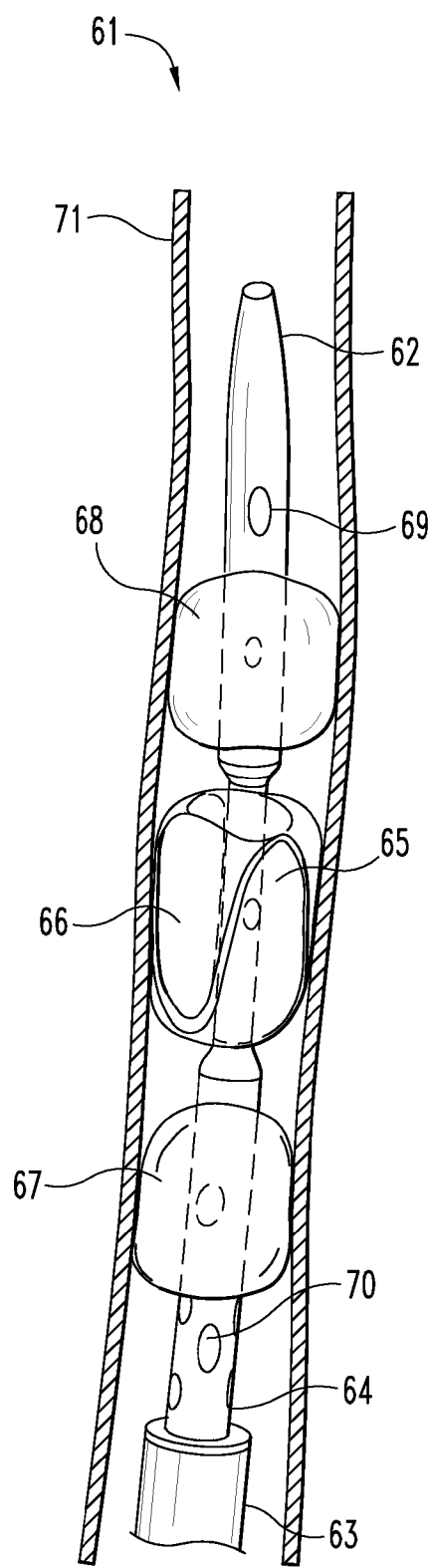
FIG. 6 provides a perspective view of another vascular valve deployment system of the invention positioned within a vascular vessel.
Figure 7:
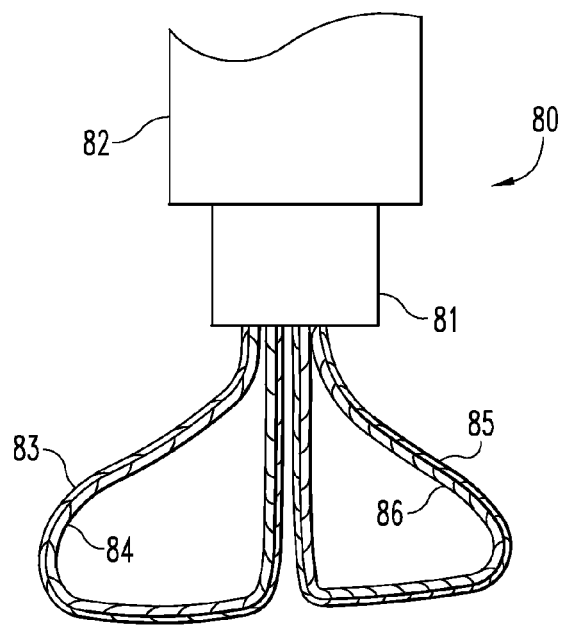
FIG. 7 provides a cut-away perspective view of a percutaneous valve material delivery device of the invention.

With reference now to FIG. 6, shown is another vascular valve deployment system 61 of the present invention. Deployment system 61 includes a delivery device 62 including an outer sheath 63 and a delivery catheter 64 receivable therein. Delivery catheter 64 includes an expandable member 65 such as an inflatable balloon (e.g. potentially similar to balloon 57 of FIG. 5), for delivery of a valve body 66 received thereon. Expandable member 65 is flanked by both a proximal occlusion element 67 and distal occlusion element 68. Occlusion elements 67 and 68 can be provided, for example, by occlusion balloons made of latex, silicone, or any other suitable material. Catheter 64 also includes one or a plurality of distal perfusion opening(s) occurring distally of distal occlusion element 68, and one or a plurality of proximal perfusion opening(s) 70 occurring proximally of proximal occlusion element 67. In use, the system 61 can be introduced into a vascular vessel 71 such as a vein, and the occlusion elements 67 and 68 can be expanded to isolate the vein segment occurring therebetween, in order to facilitate the delivery and/or attachment of the valve 66. Illustratively, the occlusion elements 67 and 68 can be expanded prior to expansion of the expandable member 65, such that when the valve 66 is deployed against the adjacent vessel wall surfaces, those surfaces will be isolated from significant blood flow. This may facilitate effective attachment of the valve body 66 to the wall using the mechanical or structural wall penetrating elements, and/or adhesives, and/or other techniques described herein. After attachment of the valve body 66 to the vessel walls, the expandable member 65 and the occlusion elements 67 and 68 can be contracted (e.g. deflated in the case of balloons), and the catheter 64 withdrawn back into sheath 63, and the sheath/catheter system withdrawn from the patient leaving in place the deployed valve body 66. In addition, it should be noted that during the time in which the vessel segment is occluded, perfusion opening(s) 69 and 70 and their associated catheter lumen can allow for perfusion of blood through the occluded segment.

With reference now to FIGS. 7-10, illustrated are additional systems and methods for percutaneously providing valves within vascular vessels. In particular, provided is a delivery system 80 including a valve body securement and delivery device 81, receivable within an outer catheter or sheath 82. Device 81 includes adaptations for releasably securing flexible material for delivery percutaneously into a vascular vessel. Specifically, in the illustrated device, provided is a first tong including closely approximated wire elements 83 and 84, and a second tong including closely approximated wire elements 85 and 86. The first and second tongs extend in paths corresponding to a desired path of attachment of flexible material to the vessel wall.

Figure 9:
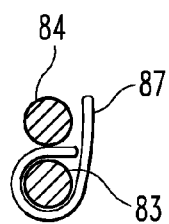
FIG. 9 provides a cross-sectional view taken along line 9-9 of FIG. 8, after tucking the flexible material, and viewed in the direction of the arrows.
Figure 8:
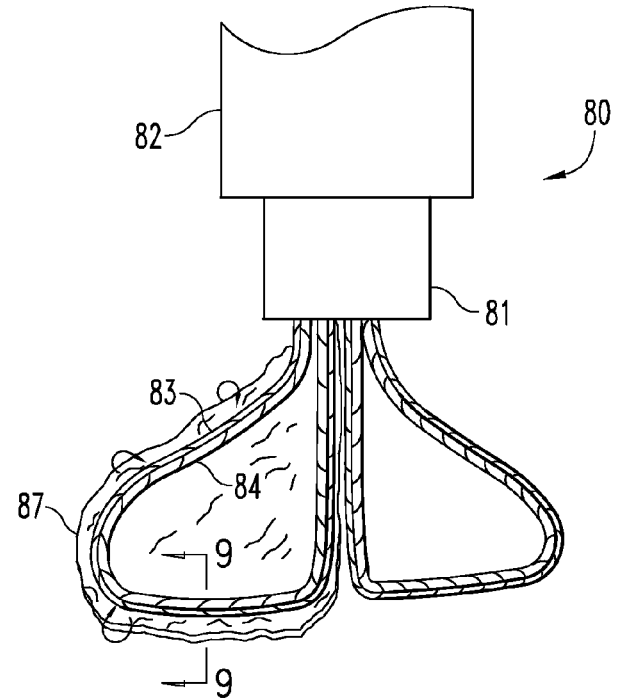
FIG. 8 provides a cut-away perspective view of one manner of securing a flexible material to the device of FIG. 7.

Referring now to FIG. 8, illustrated is one manner securing a valve-forming flexible material to a tong of delivery device 81. A sheet of flexible material 87 is positioned underneath the wire elements 83 and 84. The edges of the flexible material are then rolled inwardly (see arrows) and tucked in between wire 83 and wire 84. In this manner, the edges of the flexible material, in the desired attachment path, are received tightly between wire elements 83 and 84. In this regard, FIG. 9 shows this arrangement in a cross-sectional view taken along line 9-9 of FIG. 8 (only after tucking the edges of flexible material 87) and viewed in the direction of the arrows. It will be understood that to grip the flexible material 87, wires 83 and 84 in the tong are closely enough spaced and of a resiliency wherein they clamp and hold flexible material 87 therebetween during delivery and securement to the vessel walls.

Figure 10:
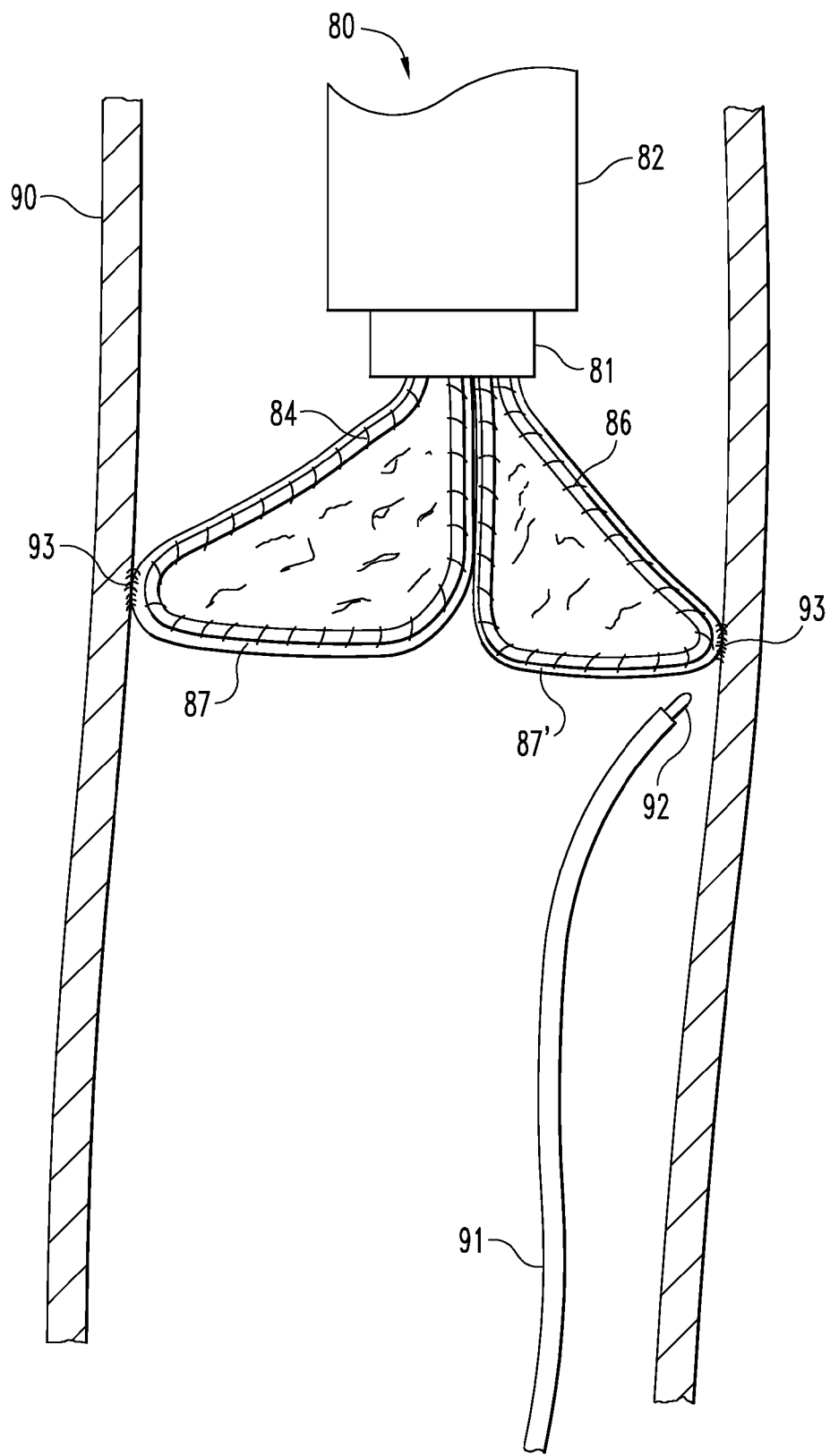
FIG. 10 provides an illustration of the use of the system depicted in FIGS. 7 through 9 in use to provide a valve within a vascular vessel.

With reference to FIG. 10, shown is an illustrative deployment of flexible material with system 80 to provide a valve within a vascular vessel 90. As shown, each tong of delivery device 81 supports a piece of flexible material (87, 87'), and upon advancement out of delivery sheath 82, the tongs move radially outward to compress portions of flexible material 87,87' against the vessel walls at least in the areas where attachment to the walls is desired. Although flexible material 87,87' can be provided by separate pieces of material, it may also be provided by a single piece of material. The flexible material 87,87' is then attached to the walls in the desired areas using any suitable means therefor. Illustratively, such means may include barbs, hooks, bonding agents, welding, staples, and any other mechanisms disclosed herein or otherwise appropriate. Illustrated in FIG. 10 is a probe 91 advanced from a separate percutaneous access, which has an energy-delivering tip 92. Probe 91 is used to deliver energy to facilitate attachment of the flexible material 87,87' to the vessel walls, for example in the shaded region designated at 93. As discussed hereinabove, the energy may function to weld the flexible material to the vessel walls and/or to activate adhesives or other substances to facilitate attachment to the vessel walls.

After attachment of the flexible material 87,87' to the vessel walls, probe 91 and system 80 can be withdrawn from the patient, leaving in place flexible material 87,87' in a structure beneficially modifying blood flow through the vessel by selectively permitting blood flow in a first direction and restricting blood flow in a second direction opposite the first direction. In this regard, optionally, to facilitate release of the flexible material 87,87', the delivery device 81 can incorporate a mechanism that can be actuated by the attending physician to separate the wires 83 and 85, and 85 and 86, to release the flexible material. For example, wires 83 and 85 can be at least partially retractable to cause such separation.

Figure 11:
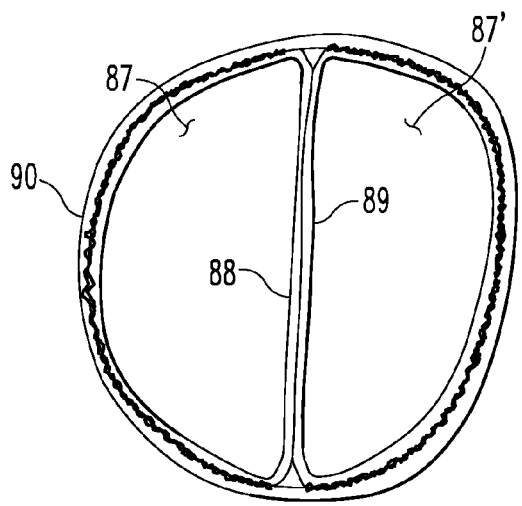
FIG. 11 provides a top view of one illustrative implanted valve of the invention.
Figure 12:
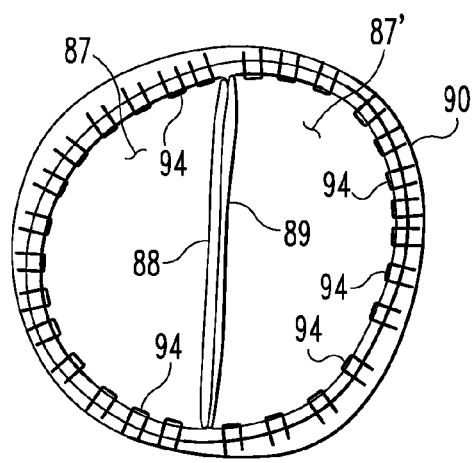
FIG. 12 provides a top view of another implanted valve of the invention.
Figure 13:
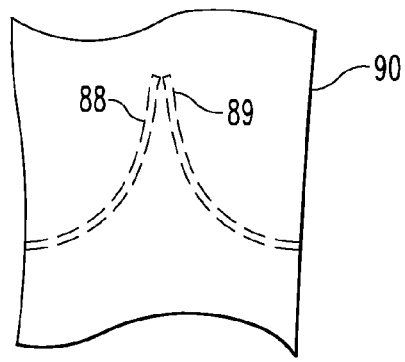
FIG. 13 provides a side view of an illustrative implanted valve of the invention.

FIGS. 11-13 are illustrative of certain flexible material configurations and attachments for providing valve function in a vascular vessel. In particular, FIG. 11 represents a top view of an implanted or engrafted valve generally in a closed condition and including flexible material 87,87' forming leaflets that provide a valving function. These leaflets have free edges 88 and 89 that move toward and away from one another to close and open, respectively, the valve orifice. As before, shaded areas 93 represent a bonded and/or welded attachment of areas of flexible material 87,87' to the wall of vessel 90. FIG. 12 provides a similar view of an implanted valve, except wherein a plurality of mechanical elements such as staples 94 is used to attach flexible material 87,87' to the vessel wall.

FIG. 13 provides a side view that could be representative of the valves in either of FIG. 11 or FIG. 12, showing a potential attachment path (in phantom) for the leaflet edges extending in a direction generally both longitudinally and circumferentially around the vessel wall, thus providing two cusp-type leaflets within the vessel 90. It will understood that these leaflet paths could be the site of attachment by any suitable means as discussed herein, including but not limited to mechanical elements, bonding, and/or welding.

Devices and systems of the invention are desirably adapted for deployment within the vascular system, and in particularly preferred embodiments, devices and systems of the invention are adapted for deployment within the venous system. Accordingly, preferred devices such as device 11 and the others illustrated are adapted as venous valves, for example for percutaneous implantation within veins of the legs or feet, to treat venous insufficiency. In this regard, the frameless nature of valves of the present invention is expected to provide advantages in venous valve function, for example in situations wherein valve function and blood flow is facilitated by adjacent muscle pumps, e.g. in the legs or feet. In these cases, the absence of any frame or support structure exerting substantial radial force upon the venous vessel will allow the vessel to collapse as in native function. As well, such frames or structures can in certain situations undesirably migrate into vessel walls, and/or cause or facilitate thrombus or embolism. The absence of such frames or structures will therefore eliminate these associated factors.

It will be understood that other valve body configurations are contemplated as being within the scope of the present invention. For example, valves disclosed in published U.S. patent application Ser. No. 777,091 filed Feb. 5, 2001, published as 20010039450 on Nov. 8, 2001, can be modified to provide valve devices and systems in accordance with the present invention (including the removal of any stent or frame elements present in the prior-disclosed valves).

It will also be understood that although certain embodiments disclosed herein have deployment systems that selectively force certain areas of the valve body material against the vessel wall, such is not necessary to broader aspects of the present invention. In particular, standard balloon or expandable devices can be used, and the flexible material of the valve body appropriately configured and adaptations applied, so as to achieve the implantation of a functional valve. For example, force can be applied essentially uniformly to a larger area of flexible material, wherein only a portion (e.g. band) of the flexible material has adaptations that facilitate its attachment to the vessel wall. For instance, attachment mechanisms such as hooks, barbs, or other wall penetrating elements, and/or adhesives or tissue-welding solders or chromophors, can be applied only to those areas for which attachment is desired. Such adaptations can be used with the embodiments disclosed hereinabove and others within the scope of the present invention. As well, it is within the scope of the present invention to deliver and lodge a valve body within a vascular vessel, withdraw the delivery system, and then in a separate, later operation, use percutaneous means as described herein to attach the valve body to the vascular vessel to provide the permanent, implanted structure. Still further, portions of the valve body delivery system (e.g. devices with expandable elements to force the valve body against the vessel walls) can be left indwelling for a period of time to allow secure attachment of the flexible material to the vessel walls, for example by tissue ingrowth in the case of flexible materials such as ECMs having remodelable properties. After secure attachment, the delivery system element can then be withdrawn.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are indicative of the abilities of those of ordinary skill in the art and are hereby incorporated by reference in their entirety as if individually incorporated by reference and fully set forth.

What is claimed is:

1. A method for modifying blood flow in a vascular vessel, the method comprising:

percutaneously delivering an implant to a site within a vascular vessel, the implant including one or more pieces of flexible material, said one or more pieces of flexible material including a first piece of flexible material which includes a reinforced peripheral region extending along an outer edge of said first piece of flexible material, said reinforced peripheral region configured to extend longitudinally along and at least partially circumferentially around a wall of the vascular vessel upon implantation and having extending therefrom an array of vessel wall-penetrating elements that is more than two vessel wall-penetrating elements wide and said array includes vessel wall-penetrating elements arranged longitudinally and generally laterally with respect to one another; and percutaneously deploying the implant in the vascular vessel so as to form a structure that selectively permits blood flow in a first direction and resists blood flow in a second direction, said percutaneously deploying including driving vessel wall-penetrating elements of said first array into a wall of the vascular vessel so as to secure said reinforced peripheral region to said vascular vessel wall with said reinforced peripheral region extending longitudinally along and at least partially circumferentially around the vascular vessel wall.

2. The method of claim 1, wherein said vessel wall-penetrating elements include barbs.

3. The method of claim 1, wherein said one or more pieces of flexible material include an adhesive applied thereto.

4. The method of claim 1, wherein said reinforced peripheral region has a thickness greater than a central portion of said first piece of flexible material.

5. The method of claim 1, wherein said vessel wall-penetrating elements include hooks.

6. The method of claim 2, wherein said barbs penetrate said first piece of flexible material.

7. The method of claim 1, wherein said first piece of flexible material has an intermediate region that extends inwardly of peripheral edges of the first piece of flexible material, said first array of vessel wall-penetrating elements extending from said intermediate region.

8. The method of claim 1, wherein said first piece of flexible material contains collagen.

9. The method of claim 1, wherein said first piece of flexible material comprises an extracellular matrix material.

10. The method of claim 1, wherein said first piece of flexible material has remodelable properties.

11. The method of claim 10, wherein said extracellular matrix material comprises submucosa.

12. The method of claim 1, wherein said structure includes a valve having two or more leaflets.

13. The method of claim 1, wherein said one or more pieces of flexible material comprise collagen, and wherein said percutaneously attaching includes delivering energy to facilitate attachment of said portions to the walls.

14. The method of claim 13, wherein said energy includes electromagnetic radiation.

15. The method of claim 14, wherein said energy is selected from microwave, radio frequency, laser, and ultraviolet light energy.

16. The method of claim 13, wherein an energy-absorbing substance is provided in contact with said portions, and wherein said energy activates the energy-absorbing substance to attach said portions to the walls.

17. The method of claim 13, wherein the energy welds said portions to the walls.

18. The method of claim 1, wherein said percutaneously delivering comprises deploying the one or more pieces of flexible material from a lumen of a percutaneously advancable device.

19. The method of claim 18, wherein said percutaneously delivering comprises deploying a delivery structure from the lumen, the delivery structure including the one or more pieces of flexible material releasably held to an expandable element.

20. The method of claim 19, wherein the expandable element includes a balloon.

21. The method of claim 18, wherein the expandable element includes a wire structure.

22. The method of claim 2, wherein said barbs include microbarbs having a diameter ranging from about 0.0005 inches to about 0.100 inches.

23. The method of claim 2, wherein said barbs include microbarbs having a diameter of up to about 0.010 inches.

24. The method of claim 23, wherein said diameter is at least about 0.005 inches.

25. The method of claim 2, wherein said barbs include microbarbs having a length ranging from about 0.001 inches to about 0.50 inches.

26. The method of claim 2, wherein said barbs include microbarbs having a length of up to about 0.100 inches.

27. The method of claim 26, wherein said length is at least about 0.01 inches.

* * * * *